US011173063B2

(12) United States Patent
Zhu

(10) Patent No.: US 11,173,063 B2
(45) Date of Patent: Nov. 16, 2021

(54) BRAIN COOLING METHOD AND PORTABLE DEVICE

(71) Applicant: Michelle Yue Zhu, Cupertino, CA (US)

(72) Inventor: Michelle Yue Zhu, Cupertino, CA (US)

(73) Assignee: Michelle Yue Zhu, Sunnyvale, CA (US)

( * ) Notice: Subject to any disclaimer, the term of this patent is extended or adjusted under 35 U.S.C. 154(b) by 604 days.

(21) Appl. No.: 15/978,152

(22) Filed: May 13, 2018

(65) Prior Publication Data

US 2019/0343678 A1 Nov. 14, 2019

(51) Int. Cl.
*A61F 7/12* (2006.01)
*A61M 16/04* (2006.01)
*A61F 7/00* (2006.01)

(52) U.S. Cl.
CPC ............ *A61F 7/12* (2013.01); *A61M 16/0461* (2013.01); *A61F 2007/0002* (2013.01); *A61F 2007/0056* (2013.01); *A61F 2007/0064* (2013.01); *A61M 2205/3606* (2013.01)

(58) Field of Classification Search
CPC ................ A61F 7/12; A61F 2007/0056; A61F 2007/0002; A61F 2007/0064; A61F 2007/0076; A61F 2007/0096; A61F 2007/0059; A61F 2007/0063; A61M 16/0461; A61M 2205/3606; A61M 16/0666; A61M 16/049; A61M 16/0066; A61M 2205/502; A61M 2210/0693; A61M 2205/8206; A61M 2210/0618; A61M 2210/0662; A61M 2230/50; A61M 2205/362; A61M 2205/3673; A61M 13/003
USPC .......................................... 607/107
See application file for complete search history.

(56) References Cited

U.S. PATENT DOCUMENTS

| | | | | |
|---|---|---|---|---|
| 2003/0094178 A1* | 5/2003 | McAuley | .......... | A61M 16/0666 128/207.18 |
| 2008/0072902 A1* | 3/2008 | Setzer | .................. | A61M 16/024 128/204.21 |
| 2011/0266999 A1* | 11/2011 | Yodfat | ............... | A61M 5/14248 320/107 |
| 2013/0030411 A1* | 1/2013 | Kreck | ................ | A61M 16/0409 604/514 |
| 2016/0058613 A1* | 3/2016 | Palazzolo | .......... | A61B 5/04017 607/105 |
| 2019/0209365 A1* | 7/2019 | Myers | ..................... | A61F 7/007 |

* cited by examiner

*Primary Examiner* — Linda C Dvorak
*Assistant Examiner* — Nils A Potter

(57) ABSTRACT

A noninvasive, brain cooling method and device for cerebral cooling via a patient's nasopharyngeal cavity, is described. Thermal conductive nasal prongs are inserted into a nasal cavity and are cooled by thermoelectric cooling elements. An outward air driving fan inside the device drives a cold air current through the nasal and oral cavities. Heat transfer between the cold air and the surface of the nasal cavity cools the nasal cavity, which in turn, cools a patient's brain. Real-time temperature sensing data provides feedback for closed-loop cooling control.

19 Claims, 3 Drawing Sheets

BRAIN COOLING METHOD AND PORTABLE DEVICE

REFERENCE CITED

U.S. Patent Document Cited

| | | |
|---|---|---|
| 9,849,025 | Dec. 6, 2017 | Zaveri |
| 9,775,741 | Oct. 3, 2017 | Barbut |
| 9,757,272 | Sep. 12, 2017 | Belson |
| 9,744,071 | Aug. 29, 2017 | Harikrishna |
| 9,737,434 | Aug. 22, 0217 | Allison |
| 9,737,103 | Aug. 22, 2017 | Preston-Powers |
| 9,717,623 | Aug. 1, 2017 | Hyogo |
| 9,629,745 | Apr. 25, 2017 | Harikrishna |
| 9,622,909 | Apr. 18, 2017 | Kulstad |
| 9,522,244 | Dec. 20, 2016 | Takeda |
| 9,445,940 | Sep. 20, 2016 | Yon |
| 9,414,959 | Aug. 16, 2016 | Belson |
| 9,375,345 | Jun. 28, 2016 | Levinson |
| 9,358,150 | Jun. 7, 2016 | Rozenberg |
| 9,320,644 | Apr. 26, 2016 | Kreck |
| 9,278,023 | Mar. 8, 2016 | Dabrowiak |
| 8,721,699 | May 13, 2014 | Barbut |
| 8,512,280 | Aug. 20, 2013 | Rozenberg |
| 8,480,723 | Jul. 9, 2013 | Barbut |
| 8,454,671 | Jun. 4, 2013 | Lennox |
| 8,313,520 | Nov. 20, 2012 | Barbut |
| 8,308,786 | Nov. 13, 2012 | Rozenberg |
| 8,303,637 | Nov. 6, 2012 | Mori |
| 8,157,767 | Apr. 17, 2012 | Rozenberg |
| 7,879,077 | Feb. 1, 2011 | MacHold |
| 7,231,771 | Jun. 19, 2007 | McMurry |
| 7,189,253 | Mar. 13, 2007 | Lunderqvist |
| 7,052,509 | May 30, 2006 | Lennox |
| 20140053834 | A1 Feb. 27, 2014 | Harikrishna |
| 20140343641 | A1 Nov. 20, 2014 | Barbut |
| 20150119962 | A1 Apr. 30, 2015 | Kulstad |
| 20180064574 | A1 Mar. 8, 2018 | Adair |

Foreign Patent Document Cited

| | | |
|---|---|---|
| RU | 2615283 (C1) | Apr. 4, 4017 |
| CN | 106038037 (A) | Oct. 26, 2016 |
| EP | 3081251 (A1) | Oct. 19, 2016 |
| UA | 101501 (U) | Sep. 10, 2015 |
| WO | 2013142365 (A1) | Sep. 26, 2013 |

Other Publication References

Boyce L W, Vliet Vlieland T P M, Bosch J, et al. High survival rate of 43% in out-of-hospital cardiac arrest patients in an optimised chain of survival. *Netherlands Heart Journal.* 2015; 23(1):20-25. doi:10.1007/s12471-014-0617-x Hagioka et al., "Nasopharyngeal Cooling Selectively and Rapidly Decreases Brain Temperature and Attenuates Neuronal Damage, Even if Initiated at the Onset of Cardiopulmonary Resuscitation in Rats," Crit Care Med 003, vol. 31, No. 10, pp. 2502-2508 (2003). cited by applicant "The RhinoChill intranasal cooling system for reducing temperature after cardiac arrest" (February 2014) Medtech innovation briefing.

CROSS-REFERENCE TO RELATED APPLICATIONS

N/A

STATEMENT REGARDING FEDERALLY SPONSORED RESEARCH OR DEVELOPMENT

N/A

THE NAMES OF THE PARTIES TO A JOINT RESEARCH AGREEMENT

N/A

REFERENCE TO SEQUENCE LISTING, A TABLE OR A COMPUTER PROGRAM LISTING COMPACT DISC APPENDIX

N/A

STATEMENT REGARDING PRIOR DISCLOSURES BY THE INVENTOR OR A JOINT INVENTOR

N/A

FIELD OF THE INVENTION

The present disclosure generally relates to cerebral cooling via the nasal cavity, oral cavity, or other parts of the body by a noninvasive method of an external source using environmental air to induce brain cooling.

BACKGROUND OF THE INVENTION

Cerebral ischemia is the lack of oxygen to the brain, often resulting in disabilities ranging from transient neurological damage to permanent brain damage. Ischemia occurs following events such as shock, heart failure, cardiac arrest, or systemic circulatory failure. During the events mentioned above, blood circulation suddenly ceases and may progress to death without intervening action. Current resuscitation technologies have prevented deaths at the scene. However, in hospitals, severe brain damage from lack of oxygen after cardiac arrest remains prominent. Annually, over one million people in the United States suffer from traumatic brain injury, which may also result in brain damage. Medical personnel and patients need a viable option to prevent brain damage after cardiac arrest and traumatic brain injury in addition to current commercially available supportive methods.

Cooling the brain to temperatures of between 32-34° C., thereby inducing mild hypothermia called "therapeutic hypothermia", has emerged to prevent brain damage after traumatic events. Research shows that hypothermia after cardiac arrest serves as a neuro-protectant to prevent damage to the brain after trauma, or when blood supply is cut off. To lower the brain temperature to desired levels, methodologies include methods of external cooling i.e., cooling helmets, blankets, etc., and invasive methods, like administering cold saline, as well as some noninvasive methods wherein cooling apparatuses are inserted into the patient's nasal, oral, or other cavities. Studies, incorporated herein as a reference, have shown that the upper area of the nasal cavity is typically only a fraction of a millimeter apart from the brain, so the nasal cavity can serve as an effective channel to cool the brain.

Current noninvasive nasopharyngeal cerebral cooling devices require large amounts of consumable supplies to operate, which result in bulky equipment and high chemical refill costs.

Additionally, current intranasal cooling devices use a plurality of chemical fluids to be sprayed into the nasal cavity, wherein evaporation of the liquid results in evaporative heat loss that cools the nasal cavity. In addition to liquid, some devices spray dry gas to accelerate the evaporation process. An example of such intranasal cooling includes, but is not limited to, the methods and devices as disclosed in U.S. Pat. No. 9,358,150. In commercial settings, RhinoChill, an intranasal cooling system has been used in emergency room and ambulance services. Patients have been treated and have demonstrated improved short and long-term brain recovery following a traumatic event. Although coolant has shown to be safe for use on humans, when it is sprayed into nasal cavities in large quantities, and possibly breathed into the lungs, it may lead to deleterious side effects. Since cooling occurs after coolant evaporates, the coolant must be continuously replenished throughout operation. As coolant evaporates, some coolant travels to and is partially acted on the nose and wasted, often resulting in frozen white noses. There is a need for energy and resource efficient cooling devices.

Devices that utilize circulation methods do not need to be continuously replenished throughout operation. In some devices, patient temperatures are passively sensed and coolant is placed in the casing of a compartment, where it circulates around the object that needs to be cooled. After the coolant absorbs heat, it flows back to the device to be cooled again. A cooling helmet can surround the skull, while circulating coolant contained in the helmet can cool the brain, as with U.S. Pat. No. 7,052,509. Although this method does not require consumable or potentially harmful chemical resources, it has multiple limitations. Cold fluid cannot easily penetrate the protective layers between the helmet and the skull. To avoid this limitation, another current device circulates chilled air throughout the nasopharyngeal cavity. In one system, pre-chilled air is sprayed into the nasal cavity through the nostrils and is exhaled through the mouth (Dohi K., Jimbo H., Abe T., Aruga T. (2006) Positive selective brain cooling method: a novel, simple, and selective nasopharyngeal brain cooling method. In: Hoff J. T., Keep R. F., Xi G., Hua Y. (eds) Brain Edema XIII Acta Neurochirurgica Supplementum, vol 96. Springer, Vienna). However, chilled air may not be available for personnel to administer to the patient outside of clinical settings.

There is a need for a device that can induce rapid hypothermia away from clinical settings, while keeping body core temperatures relatively warmer. It would be advantageous to combine current thermoelectric technology and a feedback-loop control system to achieve cerebral cooling via the nasal cavity.

SUMMARY OF THE INVENTION

This invention regards devices and methods for cerebral cooling through the nasal cavity. Lowering cerebral temperatures, thereby inducing mild hypothermia, mitigates brain damage following traumatic brain injury, strokes, sudden cardiac failures, other events that result in reduced perfusion to the brain, or treats migraines. Cerebral cooling occurs after the device drives a cold airflow through the nasal and oral cavities. Heat transfer between the upper nasal cavity and the brain results in mild brain cooling. In the following description, a cooling device inducing hypothermia is described. The device includes a control sub-system that provides for autonomous control of the patient cerebral temperatures. Among the many significant advantages of this noninvasive technology are small size, energy efficiency, mobility, accurate cerebral temperature control, and easy operation.

It is one object of the invention to provide a device for cerebral cooling, wherein thermal conductive prongs are inserted into the nasal cavity and an oral air tube is inserted into the oral cavity.

It is also an object of the invention to cool the thermal conductive nasal prongs, and provide airflow of cooled air, which enters the nasal cavity through the nostrils, and exits through the oral tube. Airflow is driven by an outward driving fan contained in the device with its outlet positioned towards the distal end of the oral tube. The nasal prongs will not obstruct air entrance into the nasal cavity. The incoming air will pass by the cold prongs and get cooled. During operation, the fan sucks air from the environment, into the nasopharyngeal cavities through the nostrils, past the cold nasal prongs, and out of the nasal and oral cavities through the oral tube. Environmental air becomes cold after it moves past the cold nasal prongs. As the air travels from the nasal cavity towards the oral tube, cold air fills and cools the entire nasal cavity.

It is a further object of the invention to cool the thermal conductive prongs by solid-state thermoelectric Peltier cooler devices contained in the device. Peltier cooler devices have the advantage of reliability, fast response time, and high heat pumping capacity. Alternatively, other kinds of cooling devices/methods can be used to cool the prongs.

It is also an object of the invention to dissipate waste heat from the hot side of the Peltier cooler through heat sinks into the environment to maintain low nasal prong temperatures.

It is another object of the invention to provide a smart control sub-system to monitor real-time cerebral temperatures and maintain operator-selected cerebral temperatures by regulating temperatures of solid-state coolers and internal fan speed.

It is a further object of the invention to provide a device wherein all aspects including the thermoelectric cooling elements, temperature sensing, and temperature control sub-system are powered by a rechargeable power source or other portable power sources, such as solar cells.

It is another object of the invention to provide a closed-loop feedback control sub-system that utilizes cerebral temperature obtained from the device's temperature sensor accessory, mounted within a support structure to be inserted into the patient's ear. This accessory sends patient cerebral temperatures measurements in real-time for the microcontroller to monitor.

It is a further object of the invention that the temperature-sensing accessory, fan, and cooling elements are connected to the microcontroller, and controlled by it, in the device.

It is also an object of the invention to provide a control sub-system wherein the microcontroller adjusts thermal electric cooler temperatures and fan speeds to maintain cerebral temperatures according to input data from the temperature sensors.

It is an objective of the control sub-system to maintain patient cerebral temperatures within the operator-selected temperature range. At the beginning of operation, and as part of the device set-up process, the operator may manually input desired temperature range into the device via the control panel.

It is an additional object of the invention that the microcontroller of the control sub-system receives user-selected target temperature range and changes thermal electric cooler temperature and fan speed according to temperature sensing input data from the temperature sensors. Accordingly, when cerebral temperature is higher than the set point, the microcontroller raises the speed of the fan, and decreases the temperature of the thermal electric cooler until cerebral temperature lowers to the operator-selected target temperature. If cerebral temperature is lower than the set-point, the fan speed is either lowered or turned off and remains in the "off" state until the temperature is higher than the set point, thereby providing a device having means for maintaining the cerebral temperature within the range selected by the operator.

It is yet another object of the invention that the control sub-system autonomously enables the device to lower and maintain cerebral temperatures without any action from the operator with the exception of battery charging, and target temperature resetting.

It is further an object of the invention to provide a device which may be easily transported between locations, and which is not unduly large or heavy.

Other objects and advantages of the present invention will be apparent in the following detailed description and the accompanying drawings.

DETAILED DESCRIPTION

The detailed embodiments of the present invention are disclosed herein. The invention is not limited to the disclosed description, which is merely exemplary of the embodiments of the invention. The invention can be embodied in different forms without departure from the principle introduced here.

Figure 1:
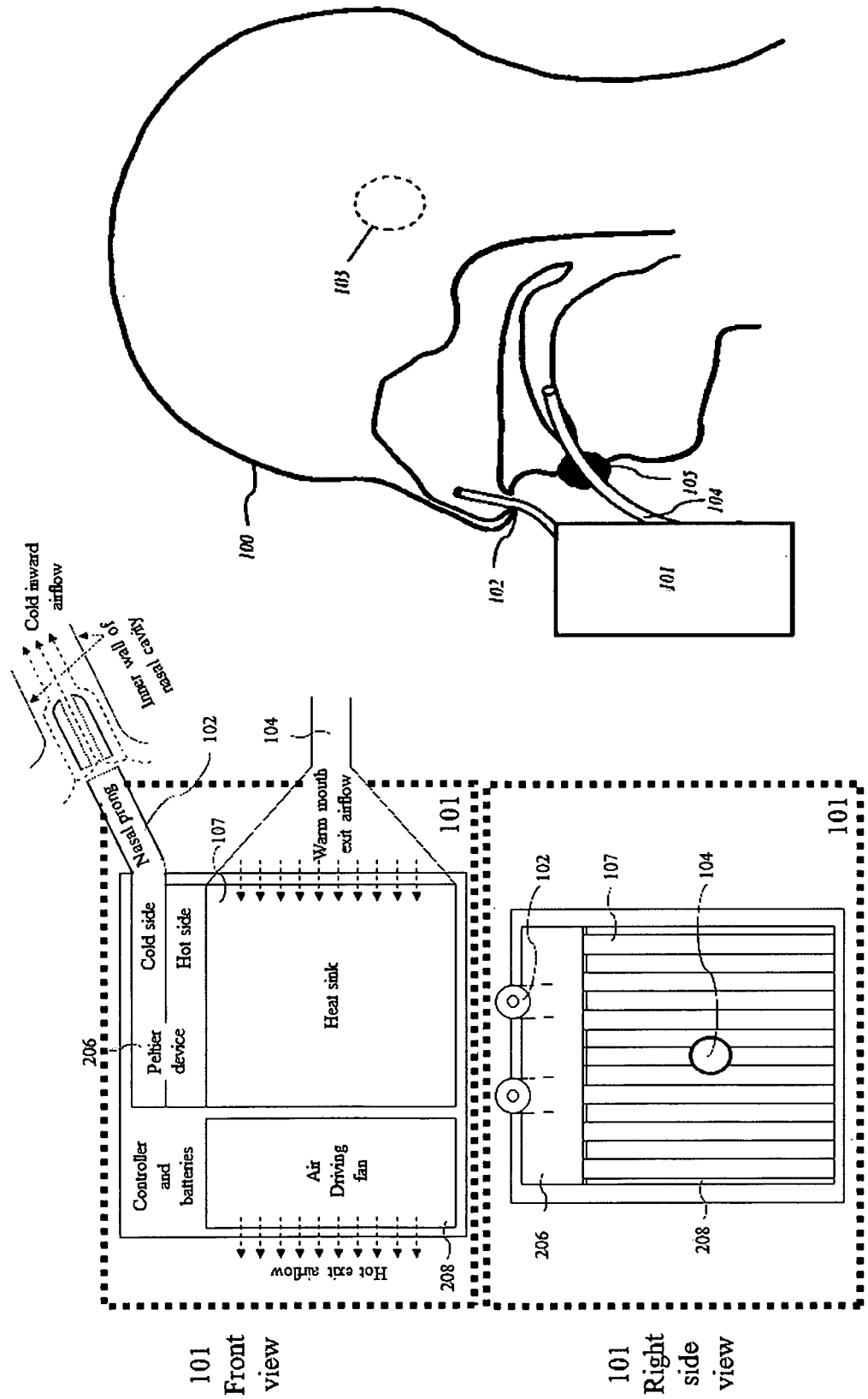
FIG. 1 illustrates the device having thermal conductive nasal prongs, and a oral tube to be inserted into the nasal and oral cavities of a patient. It also illustrates details about the device structure, including its cold nasal prongs connection to the cold side of Peltier device and heat sink connection to the hot side, airflow from inlet at the nostrils to outlet at mouth and further pass through heat sink outside the mouth to dissipate waste heat of Peltier device, all driven by the same air driving fan.
Figure 2:
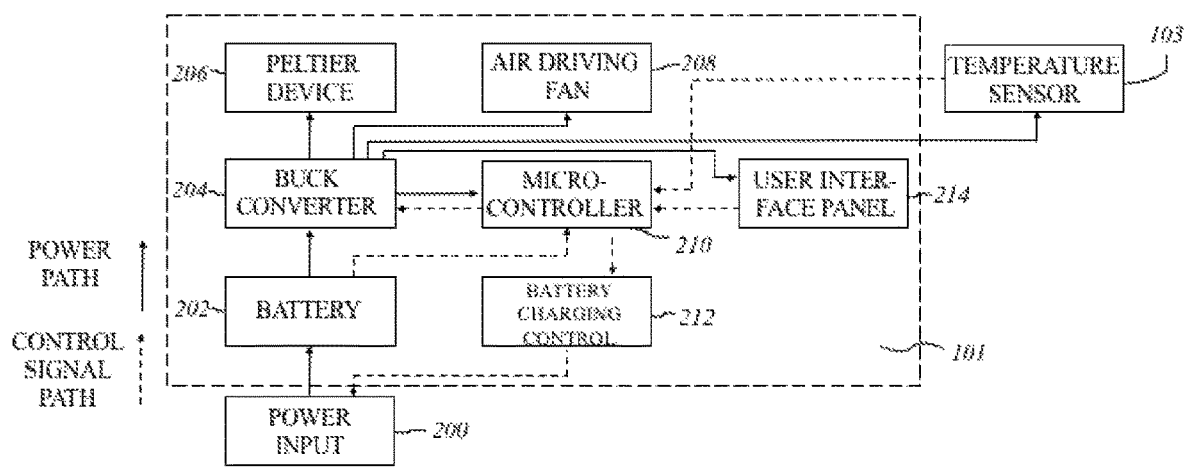
FIG. 2 illustrates the function block diagrams of the device as well as its components and parts.
Figure 3:
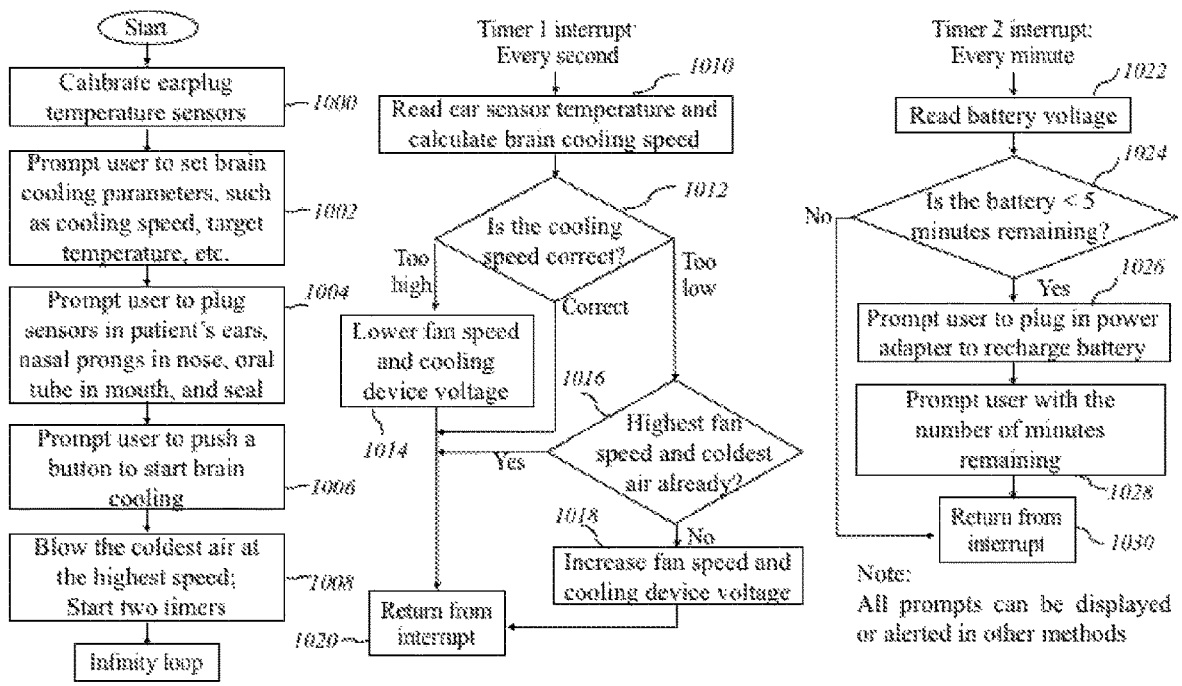
FIG. 3 is a flowchart illustrating device set-up process and an exemplary method for maintaining a patient's cerebral temperature within a target temperature range, and a method to monitor battery voltage.

In accordance with the present invention, and with reference to FIG. 1-3, a cooling device for noninvasive nasopharyngeal cerebral cooling is disclosed. One form of the invention is illustrated and is indicated in general by numeral 101. The device 101 has a cooling source composed of solid-state coolers 206, and a temperature-sensing accessory 103. These elements are coupled with nasal prongs 102, and oral tube 104 for circulation of air through the nasal and oral cavities, particularly, the upper nasal cavity. A control sub-system controls the cooling elements and monitors cerebral temperatures. As such, the microcontroller 210 receives input data from the temperature sensor 103 to regulate the speed of the cooling derive 206 and air driving fan 208 by controlling their operation voltages through buck converter 204 throughout operations.

Device 101 is illustrated in FIG. 1. with a patient 100 drawn for reference. As part of the set-up process, the operator inserts nasal prongs 102 into the patient's nasal cavity, oral tube 104 into the mouth, and ear temperature sensors 103 into the ears. Nasal prongs 102 have a smooth surface to avoid damaging tissues inside the nasal cavity. It is sized to enter the nasal cavity, and it will not obstruct air entry into the nasal cavity. The prongs 102 are illustrated vertically, though it can be tilted. It will be recognized that the length and shape of the nasal prongs may vary to maximize heat exchange efficiency and avoid patient nasal tissue damage. Oral tube 104 is sized to enter the oral cavity. The outlet of fan 208 is positioned in the device 101 at the distal end of the oral tube 104, so outward air-driving fan 208 can suck environmental air from patient's nostrils to pass the nasal and oral cavities, and into the oral tube 104. Incoming air from the nostrils is cooled after it passes the cold nasal prongs 102. When the cooled air travels towards the entrance of the oral tube 104, it fills the nasal cavity and cools the upper nasal cavity, in turn, lowering cerebral temperatures.

Nasal prongs 102 is physically connected to the cold side of Peltier device 206 and may be made from any nonreactive, and thermal conductive material, so cold from the Peltier device 206 can quickly and efficiently transfer onto the entire prong. Nasal prongs comprising of unreactive materials will not have any deleterious side effects to patients. Examples of such materials include, but are not limited to stainless steel, gold plated copper, or silver, etc.

The oral portion includes a mouth plug 105 at the end of the oral tube. The plug may be placed into the patient's mouth to cover the entrance to the oral cavity and make it air seal. It is important that mouth plug 105 covers the mouth, so environmental air can only enter the patient's nasal cavity through the nostrils. Alternatively, the mouth plug may be situated outside the patient's mouth, provided it covers the entire mouth and seals the air.

The device 101 also has temperature sensors 103 with one temperature sensor in each ear. When the temperature sensor is inserted into the ear, it will measure cerebral temperatures in real-time and send the measurement results to the microcontroller, so the microcontroller can determine how to regulate cooling device temperatures and fan speed accordingly.

Attached to the nasal prongs is a solid-state thermoelectric Peltier device 206 having fast response time, small size, and high heat pumping capability. These many advantages make Peltier devices 206 a desirable component for use in conjunction with the disclosed brain-cooling device. The Peltier device 206 and nasal prongs have an engagement surface, where the nasal prongs and the cold side of Peltier device 206 connect, so nasal prongs become cold. Electrical Peltier cooling can be adjusted to any temperature between 2° C. to the ambient temperature. In turn, the nasal prongs may be cooled to those temperatures too. A heat sink 107 is mounted on the "hot" side of Peltier device 206. The air-driving fan 208 drives the outward air to pass through the heat sink 107 to dissipate the waste heat to the environment.

As an alternative to a heat sink 107, the waste heat may be removed via circulating cooling fluid, any other method of absorbing heat, or dissipating heat for the purpose of conveying waste heat away from the "hot" side of the Peltier device 206. The air driving fan blows the airflow through the heat sink 107 of the Peltier device 206 so the waste heat generated by the air driving fan and Peltier device 206 will be expelled along with the air flow into the environment without heating up the nasal and oral cavities.

Battery 202 provides energy for the cooler, air driving fan, temperature sensors and other control elements used in this invention. Any batteries that pose no hazardous, caustic, combustible threat, nor cause undo risks if casings are ruptured or damaged are suitable for this device. Alternatively, the device can run on any other power source used in accordance with the invention, for example a solar cell panel that can provide power at remote locations.

After battery drain, external power 200 is connected to this device to recharge the battery 202. The battery charging control 212 includes a power converter that automatically converting input voltages to a suitable DC level for battery recharging. The microcontroller 210 in the control subsystem controls battery charging process from start to end.

In another object of the invention, a smart control sub-system regulates nasal prong temperature, fan speed, and in turn, patient brain temperature with the minimum energy consumption. During operation, the microcontroller 210 inside the device receives real-time temperature data measured by the temperature sensors 103 and responds accordingly. The microcontroller 210 adjusts fan 208 speed from low to high settings and regulates nasal prong temperatures by controlling the input voltage to the Peltier device 206. Controlling Buck converter 204 outputs allows the microcontroller to effectively switch between the above-mentioned settings to maximize efficiency, and prolong battery life. Alternatively, Buck converter 204 may be replaced with another means of regulating cooler temperature and fan speed.

The functions of the microcontroller are herein detailed. The microcontroller records commands from the user after he or she selects a temperature range via user interface panel 214. The microcontroller receives temperature measurement results from the temperature sensors 103 and adjusts buck converter outputs to regulate fan speed and Peltier cooler temperature accordingly. The microcontroller is also capable of supportive functions 212 including battery overheat prevention, battery charge or discharge control, as well as DC-DC converter operations used in battery recharging. To ensure safety of batteries, the microcontroller monitors battery pack output current and temperatures continuously. Any abnormal output current increase and/or battery temperature rise will cause the microcontroller to cut off the batteries completely to prevent battery overheat. The microcontroller is programmable, hence can be programmed to perform additional functions not disclosed here.

As depicted in the flowchart illustrated in FIG. 3, a microcontroller regulates the device cooler temperatures, and battery status when used in conjunction with temperature sensors and user-interface. This control sub-system may include continuous time interrupts at pre-determined intervals to automatically regulate internal functions. For maintaining cerebral temperatures, the device analyzes real time brain temperature at every interval and determines how to regulate voltage to the cooler and fan until brain temperature reaches the target temperature including automatically stopping delivery of the airflow onto the surface of the patient's nasal cavity when the patient's brain temperature reaches the target temperature range, and resuming delivery of the airflow when the patient's brain temperature rises more than a preselected tolerance above the target temperature range, and then maintain the temperature range until the patient is transferred to hospital where systematic brain cooling method will be used.

As shown in FIG. 3, in operation initialization step 1000, the device starts and calibrates temperature sensors. At step 1002, the microcontroller control panel displays a message to prompt the user to set brain cooling parameters, which may include a target cerebral temperature, and/or specific cooling patterns to accommodate unique patient cases. For example, as depicted in step 1008, the default airflow setting can be the lowest or the highest speed, but it can change as the operator sees fit. After the operator inserts the nasal prongs into the patient's nose, oral tube into patient's mouth and seal it, and plugs temperature sensors into the patient's ear at step 1004, the device is ready for operation. At step 1006, the device prompts the operator to push the start button to initiate brain cooling. At step 1008, the device is turned on and begins to circulate the coldest air at the highest speed, while simultaneously starting two interrupt timers. The following steps are in infinity loops.

Timer 1 interrupt service subroutine step 1010 starts the closed-loop control sub-system, which operates at every one-second interval. Every second, Timer 1 interrupts the microcontroller function and analyze the temperature sensor measurement against the target temperature. Then, the device calculates the present brain cooling speed. At step 1012, the microcontroller analyzes the difference between present and the target brain temperatures to calculate the optimal brain cooling speed to reach/maintain the desired temperature. The microcontroller determines whether the present cooling speed is right, or too high, or too low. If the temperature reading value is lower than the target temperature, the microcontroller determines the present cooling speed is "too high" and proceeds to step 1014. At step 1014, the microcontroller decreases voltages to the fan and cooling device to lower fan speed and increase cooler temperature. Alternatively, the microcontroller may turn off voltage to the fan and Peltier cooler entirely until the next interrupt. Conversely, at step 1012, if the brain temperature is higher than the target temperature, then the cooling speed is too low and the device proceeds to step 1016. If the fan speed and cooler setting is not at the highest/coldest, the microcontroller will increase the voltage to these elements, as depicted at step 1018. If the fan speed and cooler temperature is already at their highest settings, the microcontroller will maintain the highest setting and revert back to step 1020, until temperature is again measured and found to be at the target temperature. At step 1012, the microcontroller may determine that the cooling speed is "correct" and the voltages to the cooling and fan elements stay the same until the next time interrupt at step 1020.

As mentioned above, the control sub-system has a supportive function of monitoring battery voltage. The microcontroller also provides means of informing the operator when battery voltage is low. This is shown by the sequence following step 1022. Timer two interrupts the microcontroller every minute. At step 1022, the microcontroller reads the battery voltage and determines if the battery has less than 5 minutes of operation time remaining. If the device has more than 5 minutes of battery capacitance remaining, it returns to normal operation from the interrupt. If the battery has less than 5 minutes of operation time remaining 1024, the microcontroller will proceed to step 1026 and prompt the user to plug in the power adapter to recharge the battery, and display the operation time remaining before the device returns from interrupt.

In summary, the embodiments of the device disclosed herein may be used for a plurality of potential uses and implementation, among which mitigation of brain damage after cardiac arrest and traumatic brain injury in out-of-hospital settings is the function discussed above. The energy efficient aspects of the invention allow the overall device to be small in size, light in weight, and easy to use. These advantages are especially important in emergency operational settings. In combination with a smart feedback control sub-system, the device is reliable and can be used without highly specialized operators.

What is claimed is:

1. A noninvasive cooling method for brain damage prevention, comprising following steps:
    inserting nasal prongs into a nasal cavity of a patient through nostrils, the nasal prongs comprising a thermal conductive surface;
    inserting an oral tube into an oral cavity of the said patient through a mouth of the said patient, the oral tube is a hollow member comprising a proximal end, a distal end, and an outward air driving fan positioned at the distal end;
    the said outward air driving fan configured to pull an airflow into the said patient's nostrils, through the nasal cavity, and then the oral cavity, and exit through the said oral tube;
    the said nasal prongs connected to a cold side of a solid state cooling element, or other alternative of cooling devices, providing a cooling source to the said airflow; the said airflow passing through the said cold nasal prongs, being cooled through heat exchange with the cold exterior and hollow interior surface of the said nasal prong; inserting temperature sensors into the said patient's ears;
    delivering the airflow onto a surface of the said patient's nasal cavity through the cold exterior and hollow interior surface of the nasal prongs for a period of between minutes to hours;
    wherein the airflow is circulated within the nasal and oral cavities and wherein the airflow exchanges heat with the surface of a nasal cavity to reduce a cerebral temperature of the said patient to a protective temperature range;
    the airflow further passing through an oral cavity and exiting through the oral tube.

2. The method of claim 1, wherein the airflow is environmental air, oxygen, or other suitable gas.

3. The method of claim 1, wherein the step of pulling the airflow into the said patient's nostrils further comprises: delivering a moderate cold air first to reduce a patient's cerebral temperature moderately and delivering a colder air subsequently to further reduce the patient's cerebral temperature to within the protective temperature range.

4. The method of claim 3, wherein the step of delivering the moderate cold air is administered to maintain the patient's cerebral temperature within the protective temperature range to prevent rewarming of the cerebral temperature of the patient.

5. The method of claim 4, further comprising repeating the step of delivering the moderate cold air onto a surface of a patient's nasal cavity through the patient's nostrils and the cold nasal prongs for the period of between minutes to hours to maintain the reduced cerebral temperature or prevent rewarming during transition to a systemic cooling method.

6. The method of claim 5, wherein the method occurs for a period of time, ranging from minutes to hours during a transitioning of the patient from nasal cooling to other systemic cooling methods.

7. The method of claim 1, wherein the airflow is cooled by a solid state cooling element or other alternative cooling devices or their combinations.

8. A noninvasive cooling method for brain damage prevention, comprising:
    inserting nasal prongs into a nasal cavity of a patient through nostrils, the nasal prongs comprising a thermal conductive surface;
    inserting an oral tube into an oral cavity of the said patient through a mouth of the said patient, the oral tube comprising a proximal end, a distal end, a hollow member, and an outward air driving fan positioned at the distal end;
    the said outward air driving fan configured to pull an airflow into the said patient's nostrils, through the nasal cavity, and then the oral cavity, and exit through the said oral tube;
    the said nasal prongs connected to a cold side of a solid state cooling element, or other alternative cooling devices, providing a cooling source to the said airflow; the said airflow passing though the said cold nasal prongs, being cooled through heat exchange with the cold exterior and hollow interior surface of the said nasal prong;
    inserting temperature sensors into the said patient's ears;
    delivering an airflow onto a surface of the patient's nasal cavity through an exterior and a hollow interior cold surface of the nasal prongs for a period of between minutes to hours; wherein the airflow circulates within the nasal and oral cavities and wherein the airflow exchanges heat with the surface of the nasal cavity to reduce a cerebral temperature of the patient to a protective temperature range;
    measuring the patient's brain temperature; and
    adjusting delivery of the cold airflow in response to the patient's brain temperature measurement results.

9. The method of claim 8, further comprising adjusting a temperature of the solid state cooling element or other alternative cooling devices and a speed of the outward air driving fan.

10. The method of claim 8, further comprising stopping and resuming the step of delivering the airflow onto the surface of the patient's nasal cavity, passing the airflow through the cold surface of nasal prongs for a period of time from between minutes to hours to prevent rewarming of a patient's brain.

11. The method of claim 8, wherein measuring the patient's brain temperature further comprises measuring the patient's cerebral temperature through the temperature sensors in the patient's ears.

12. The method of claim 8, wherein the step of measuring the patient's brain temperature further comprises continuously monitoring the patient's brain temperature through the temperature sensors in the patient's ears.

13. The method of claim 8, further comprising a step of setting a target temperature range for the brain cooling, wherein the step of delivering the airflow further comprises delivering the airflow onto the surface of the patient's nasal cavity until the brain temperature reaches the target temperature range.

14. The method of claim 13, further comprising automatically stopping delivery of the airflow onto the surface of the patient's nasal cavity when the patient's brain temperature reaches the target temperature range, and resuming delivery of the airflow when the patient's brain temperature rises more than a preselected tolerance above the target temperature range.

15. The method of claim 13, wherein the target temperature range is set by an operator.

16. A brain cooling air channel comprising:
air cooling prongs for insertion into nostrils forming an intake or entrance of the air channel;
the air cooling prongs for providing an airflow flowing into a nasal cavity and exchanging heat with a surface of the nasal cavity to remove heat from the brain to reduce a cerebral temperature;
an air outlet tube configured to be positioned at a mouth for providing a seal of the mouth to form an exit of the air channel;
an outward air driving fan at the exit of the air channel to drive the airflow inside the air channel through suction, the said outward air driving fan configured to pull an airflow into the nostrils, through the nasal cavity, and then the oral cavity, and exit through the said air outlet tube;
the said air cooling prongs connected to a cold side of a solid state cooling element, or alternative cooling devices, for providing a cooling source to the said airflow; the said airflow passing though the said air cooling prongs, being cooled through heat exchange with a cold exterior and hollow interior surface of the said air cooling prongs.

17. The air driving fan of claim 16 configured to drive the airflow through a heat sink of a solid state cooling element to dissipate waste heat from the solid state cooling element or alternative cooling devices.

18. A device implementing the brain cooling air channel of claim 16, comprising supporting hardware components:
a controllable cooling source comprising a solid state thermal electric cooling element or other alternative cooling devices to cool the airflow to a desired temperature range; an airflow driver comprising an air driving element to drive airflow flowing from the nostrils through a nasal cavity and then an oral cavity to a mouth and exit to the environment through a heat sink, dissipating waste heat generated by the cooling element;
a controllable voltage source comprising Buck converters to generate a required voltage to power the thermal electric cooling element to different cooling temperatures, and to generate the required voltage to drive the air driving element to operate at a different speed;
a power source providing power to the device to operate independently without an external power source for a certain length of time;
a brain temperature measurement element comprising temperature sensors for measuring a brain temperature in real time;
a control element comprising a microcontroller receiving device operation parameters set by operators to control an operation of said brain cooling device.

19. The power source of claim 18 comprising a rechargeable battery or other portable power sources to maintain portability of the device.

* * * * *